(12) United States Patent
Tazoe et al.

(10) Patent No.: US 7,749,205 B2
(45) Date of Patent: Jul. 6, 2010

(54) AUTOMATIC URINE DISPOSAL DEVICE AND URINE RECEPTACLE USED THEREFOR

(75) Inventors: Wataru Tazoe, Tsuchiura (JP); Junichi Kobayashi, Ushiku (JP); Ryousuke Miyagawa, Kasukabe (JP); Kenji Yoshida, Nagoya (JP); Shigeru Machida, Iwama (JP); Ichiro Wada, Toyohama (JP); Miou Suzuki, Toyohama (JP); Kenichi Okabe, Chiyoda (JP)

(73) Assignees: Hitachi, Ltd., Tokyo (JP); Uni-Charm Corporation, Kawanoe-shi (JP)

( * ) Notice: Subject to any disclaimer, the term of this patent is extended or adjusted under 35 U.S.C. 154(b) by 0 days.

(21) Appl. No.: 10/796,025

(22) Filed: Mar. 10, 2004

(65) Prior Publication Data

US 2004/0236292 A1 Nov. 25, 2004

(30) Foreign Application Priority Data

Mar. 10, 2003 (JP) .............................. 2003-063455

(51) Int. Cl.
*A61M 1/00* (2006.01)
(52) U.S. Cl. ......................... 604/320; 604/317; 604/319
(58) Field of Classification Search ................. 604/313, 604/317, 329, 331, 319, 320
See application file for complete search history.

(56) References Cited

U.S. PATENT DOCUMENTS

| | | | | |
|---|---|---|---|---|
| 3,520,305 A * | 7/1970 | Davis | .......................... | 604/349 |
| 3,721,243 A * | 3/1973 | Hesterman et al. | ............ | 604/67 |
| 4,345,341 A * | 8/1982 | Saito | .............................. | 4/301 |
| 4,449,971 A * | 5/1984 | Cawood | ..................... | 604/544 |
| 4,631,061 A | 12/1986 | Martin | | |
| 4,846,816 A * | 7/1989 | Manfredi | ..................... | 604/323 |
| 4,886,508 A * | 12/1989 | Washington | ................ | 604/327 |
| 4,889,533 A * | 12/1989 | Beecher | ...................... | 604/330 |
| 4,892,527 A * | 1/1990 | Zivny | ......................... | 604/353 |
| 4,994,051 A * | 2/1991 | Walsh | ........................ | 604/349 |
| 5,002,541 A * | 3/1991 | Conkling et al. | ............ | 604/319 |
| 5,053,027 A * | 10/1991 | Manfredi | ..................... | 604/327 |
| 5,267,989 A * | 12/1993 | Moyet-Ortiz | ............... | 604/349 |
| D358,467 S * | 5/1995 | Davis, Sr. | .................. | D24/118 |
| 5,411,495 A * | 5/1995 | Willingham | ................ | 604/329 |
| 5,451,217 A * | 9/1995 | Fujioka et al. | .............. | 604/378 |
| 5,678,564 A * | 10/1997 | Lawrence et al. | ........... | 600/574 |
| 5,701,612 A * | 12/1997 | Daneshvar | .................. | 4/144.3 |
| 5,787,843 A * | 8/1998 | Chao | .......................... | 119/869 |
| 5,911,222 A * | 6/1999 | Lawrence et al. | ........... | 600/574 |
| 6,132,408 A * | 10/2000 | Lutz | ............................ | 604/335 |

(Continued)

FOREIGN PATENT DOCUMENTS

GB 2244653 12/1991

(Continued)

*Primary Examiner*—Melanie J Hand
(74) *Attorney, Agent, or Firm*—Antonelli, Terry, Stout & Kraus, LLP.

(57) ABSTRACT

A wearer wears a urine receptacle in which a urine absorbent material 3 is housed in a substantially rectangular, non-breathable, liquid-impermeable outer sheet having a U-shaped cross-section, and the surface of the urine absorbent material is covered with a hard-breathable, liquid permeable top sheet. Urine is discharged from a urine drainage port formed on the bottom surface of the outer sheet to a sealed urine tank by a vacuum pump through urine drainage tubes.

3 Claims, 7 Drawing Sheets

U.S. PATENT DOCUMENTS

| | | | |
|---|---|---|---|
| 6,223,751 B1 * | 5/2001 | Park | 128/885 |
| 6,370,701 B1 * | 4/2002 | Siegrist | 4/144.1 |
| 6,471,680 B1 * | 10/2002 | Cawood | 604/327 |
| 6,493,883 B2 * | 12/2002 | Jones | 4/144.1 |
| 6,635,037 B1 * | 10/2003 | Bennett | 604/349 |
| 6,709,409 B2 * | 3/2004 | Vella | 600/573 |
| 6,723,078 B1 * | 4/2004 | Pennington et al. | 604/327 |
| 6,736,803 B2 * | 5/2004 | Cawood | 604/327 |
| D496,099 S * | 9/2004 | Bisbee | D24/118 |
| 6,887,223 B2 * | 5/2005 | Bisbee | 604/353 |
| 2002/0062114 A1 * | 5/2002 | Murai et al. | 604/385.01 |

FOREIGN PATENT DOCUMENTS

| | | |
|---|---|---|
| JP | 07-171182 | 7/1995 |
| JP | 11-113946 | 4/1999 |
| WO | 9309736 | 5/1993 |
| WO | WO 9608223 A1 * | 3/1996 |

* cited by examiner

AUTOMATIC URINE DISPOSAL DEVICE AND URINE RECEPTACLE USED THEREFOR

BACKGROUND OF THE INVENTION

The present invention relates to an automatic urine disposal device of the type worn by the bedridden elderly, hospitalized patients, physically disabled people, and others who are unable to voluntarily control their bladder or to clean up urine on their own, and it also relates to a urine receptacle to be used therefor.

Because of age, physical disability, hospitalization due to injury or illness, or other physical conditions, people sometimes become unable to voluntarily control their bladder or clean up urine on their own. In those situations, a catheter is directly inserted into the bladder to allow urine to discharge into a receptacle, or a paper diaper is used.

When a catheter is directly inserted into the bladder, the wearer feels great discomfort, and there is also the probability that the urethra or bladder may be injured, and the occurrence of an infection is likely. Thus, expertise as well as special, sterilized utensils are required.

When a paper diaper is worn for a prolonged period of time, on the other hand, urine may leak, the wearer can become uncomfortable, feel stuffy, or experience skin troubles, such as rashes. To avoid this, the paper diaper must be frequently changed, which will impose a considerable physical and mental burden on both the wearer and the caretaker. Imposed on a daily basis, those physical and mental burdens become a big concern and a significant economical burden as well.

To avoid those problems, an approach has been taken in which urine that has been absorbed by a urine absorbent material, which is in the form of a thick liquid-absorbent sheet encased in the main portion of a urine receptacle, is discharged by a vacuum pump and directed to a urine tank.

The vacuum pump absorbs air in a sealed urine tank; and, due to the pressure difference between the tank's pressure and the atmospheric pressure, urine absorbed in the urine absorbent material is drained through the urine drainage tube into the urine tank. Automatic urine disposal devices having such a configuration are disclosed, for instance, in Japanese Patent Laid-Open No. Hei 07-171182 and Japanese Patent Laid-Open No. Hei 11-113946.

In the conventional devices, the urine receiving surface of the urine absorbent material, which is a surface that comes in contact with a wearer's urinating part, is exposed to air. This situation causes air to be absorbed together with urine, which decreases the urine absorbent efficiency of the device. For this reason, the amount of urine which remains in the urine receptacle (urine absorbent material) is large, which makes the wearer feel uncomfortable. To reduce the amount of urine which remains in the urine receptacle, the capacity of the vacuum pump must be increased. Accordingly, it becomes necessary to increase the size and volume of the urine disposal device.

As stated above, in the conventional devices, the amount of urine which remains in the urine receptacle is large, and the reduction of such a volume of urine requires a large and heavy urine disposal device.

SUMMARY OF THE INVENTION

An object of the present invention is to provide a compact and lightweight automatic urine disposal device in which the percentage of urine collection by the urine receptacle is increased, and also to provide a urine receptacle for use therewith.

The present invention is designed to use a urine receptacle in which a urine absorbent material is housed in a substantially rectangular, non-breathable, liquid-impermeable outer sheet having a U-shaped cross-section, and the surface of the urine absorbent material is covered with a non-breathable top sheet. The urine is discharged from a urine drainage port formed on the bottom surface of the outer sheet to a sealed urine tank by a vacuum pump through a urine drainage tube.

In other words, in accordance with the present invention, the urine absorbent material is housed in a non-breathable, liquid-impermeable outer sheet, and a hard-breathable, liquid-permeable top sheet, which stretches between both upper ends of the outer sheet's edge portions (end portion), covers the urine absorbent material. Thus, the outer sheet together with the top sheet keeps the urine absorbent material highly airtight, and a vacuum pump decreases air pressure in the urine absorbent material, thereby directing urine from a urine drainage port in the outer sheet to a urine tank through a urine drainage tube.

In the urine receptacle of the present invention, the urine absorbent material is housed in both the outer sheet and the top sheet in a space which is kept highly airtight. Therefore, as air pressure in the urine absorbent material decreases, the urine absorbent material is compressed, causing urine to be squeezed out. As a result, the percentage of urine collection increases, and the amount of urine which remains in the urine receptacle is reduced. With the increase in the percentage of urine collection, a small capacity vacuum pump with a low power can drain urine from the urine absorbent material. Therefore, it is possible to drain urine from the urine receptacle without discomfort to the wearer, and the device can be both compact and lightweight.

DETAILED DESCRIPTION OF THE PREFERRED EMBODIMENTS

Figure 1:
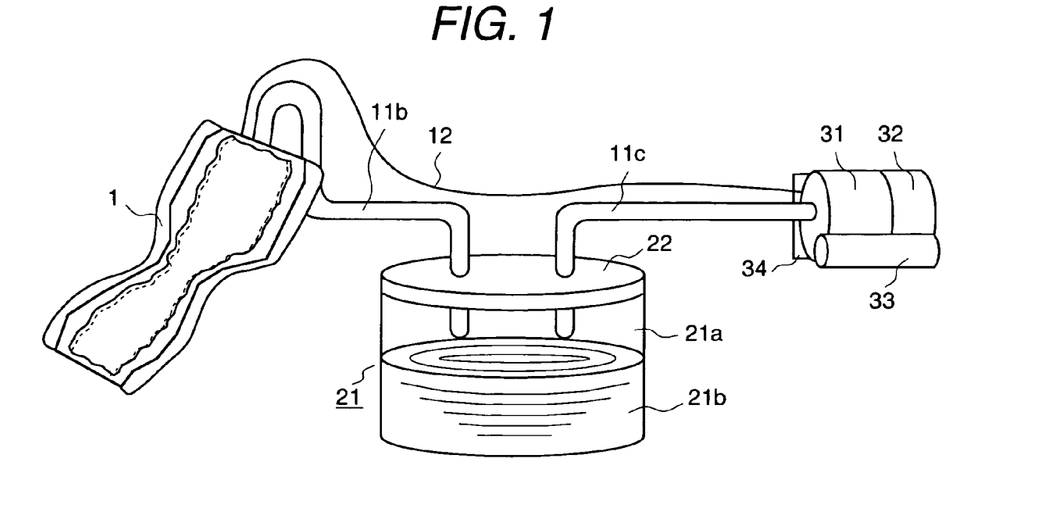
FIG. 1 is a diagram showing the automatic urine disposal device according to an embodiment of the present invention.

FIGS. 1 through 4 are directed to one embodiment of the present invention. FIG. 1 shows an example of the automatic urine disposal device according to the present invention and FIGS. 2(a) and 2(b) show a urine receptacle, for use therein.

In FIGS. 1 through 4(a), a urine receptacle 1, which absorbs urine that is discharged from a wearer's urinating part, is substantially rectangular, and its width at the middle portion in the longitudinal direction is narrow, so that it is shaped like an hourglass. The urine receptacle 1 comprises a top sheet 2, urine absorbent material 3, an outer sheet 4 and gathers 5. The top sheet 2 is made of a soft, flexible material, such as a non-woven fabric. The urine absorbent material 3, outer sheet 4 and gathers 5 are also made of soft, flexible materials.

Figure 2A:
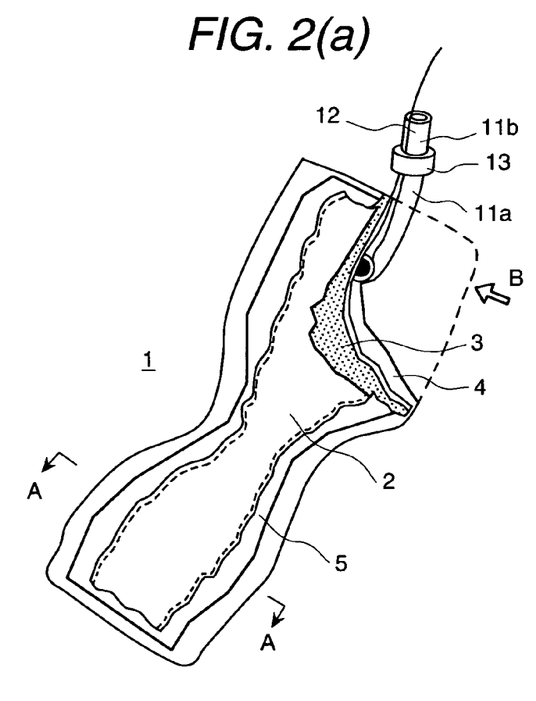
FIG. 2(a) and FIG. 2(b) are diagrams showing an embodiment of the urine receptacle.
Figure 2B:
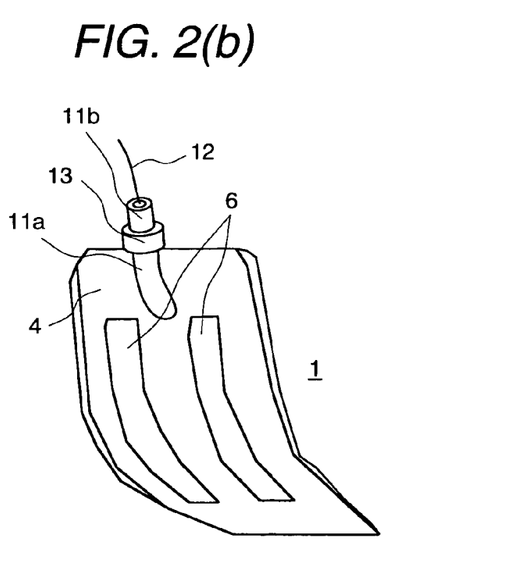

As shown in FIG. 2(a) and FIG. 2(b), the outer sheet 4, which is a component of the urine receptacle 1, is substantially rectangular, and its width at the middle portion in the longitudinal direction is narrow, so that it is shaped like an hourglass. The reason for this shape is to fit the wearer's crotch.

Figure 3:
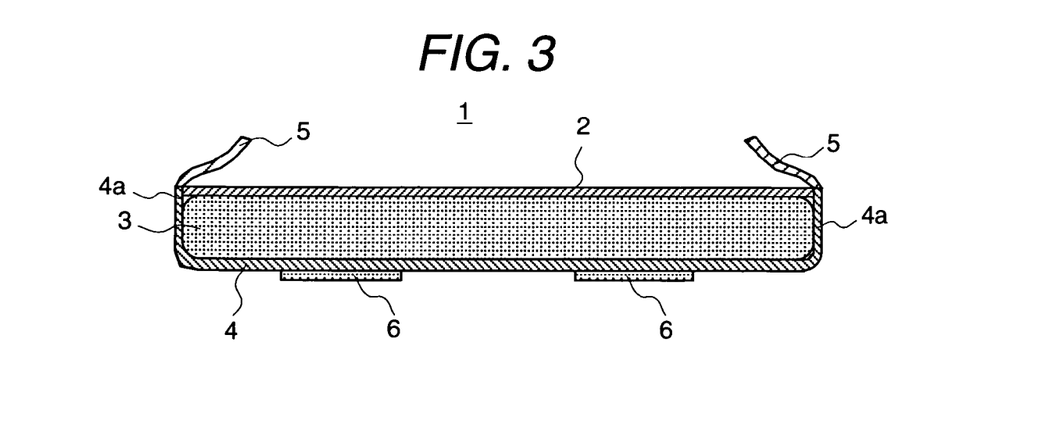
FIG. 3 is a sectional view taken substantially along the line A-A in FIG. 2(a).
Figure 4A:
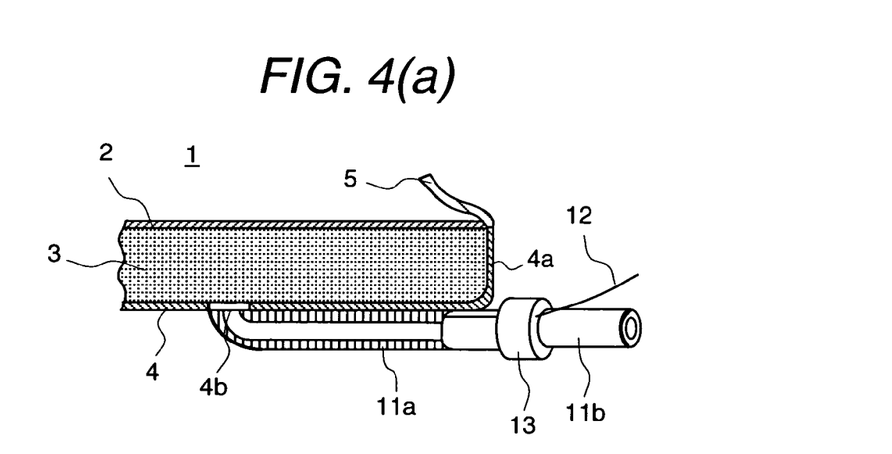
FIG. 4(a) and FIG. 4(b) are sectional views taken in the direction of arrow B in FIG. 2.

As shown in FIG. 3, the cross-section of the outer sheet 4 in the width direction shows a forked shape, and a urine drainage port 4b is formed on the bottom surface, as shown in FIG. 4(a). The cross-section of the outer sheet 4 in the longitudinal direction also has a forked shape, as shown in FIG. 3, although the size is different. The edge portion (end portion) 4a is formed along the outer periphery of a substantially rectangular outer sheet 4.

The outer sheet 4 is a liquid-impermeable, non-breathable thin sheet, and it is made of polyethylene film, for example. The outer sheet 4 is 200 to 300 mm long and 50 to 100 mm wide. The outer sheet 4 may be simply made of a liquid-impermeable, non-breathable member; however, more desirably, an optimal member can be chosen by taking into account the stuffiness which may result from prolonged use. The outer surface of the outer sheet 4 is laminated with a soft and smooth surface material (not shown), such as a polypropylene non-woven fabric, to prevent the wearer from becoming uncomfortable. The inner surface of the outer sheet 4 has been treated with a water-repellent material.

A urine absorbent material 3 is housed in the outer sheet 4, and a liquid-permeable, hard-breathable top sheet 2 covers the surface (upper surface) of the urine absorbent material 3. The top sheet 2 is adhered to both upper ends of the edge portions (end portion) 4b of the outer sheet 4, and the outer sheet 4 together with the adhered top sheet 2 maintains the urine absorbent material 3 in a highly airtight condition.

Herein, hard breathability of the top sheet 2 means that the breathability measured according to the General Textile Testing Method's breathability testing method A, prescribed in JIS L 1096, 6.27.1, is from 0 to 100 $cm^3/cm^2$/second, and more preferably, from 0 to 50 $cm^3/cm^2$/second, when the top sheet 2 is moist. When the top sheet 2 is dry, the breathability is from 20 to 200 $cc/cm^2$/second, preferably, from 20 to 100 $cc/cm^2$/second, and, more preferably, from 20 to 50 $cm^3/cm^2$/second.

Herein, "being moist" is a condition in which the moisture content (%) of the top sheet 2 that is obtained by the following Equation 1 is 100% or more, and "being dry" is a condition in which the top sheet 2 has been left dry in a 20° C. and RH 60% atmosphere, or the condition of, what is called, official moisture regain.

Moisture content=(Weight of moist sheet−Weight of dry sheet)/(Weight of dry sheet) (Equation 1)

The urine absorbent material 3 is 5 mm thick and is designed to absorb approximately 500 $cm^3$ of urine. The ability to absorb 300 $cm^3$ of urine is adequate for holding one urination of one average adult. However, a good safety margin is provided for the amount of urine to be absorbed in the material by allowing for a decrease in urine absorption of the urine receptacle 1 due to pressure applied to the urine receptacle 1 when a wearer is seated, causing the urine receptacle 1 to be pressed between the wearer's body and the seating surface, or an increase in pressure as a result of the wearer closing his/her legs and sandwiching the urine receptacle 1.

The top sheet 2 is made of a liquid-permeable, hard-breathable non-woven fabric that is made of, for example, polypropylene and polyolefin polyester blended with cotton, so that friction between the wearer's skin and the fabric is minimized. In addition, a mesh sheet makes up a part of the surface of the non-woven fabric that is used as the top sheet 2 where it comes in contact with the wearer's urinating part and the surrounding skin. This is to increase the liquid-absorbent and sweat-absorbent capabilities, so that urine can be quickly absorbed by the absorbent material 3 through small pores created in the mesh sheet. Because urine can be quickly absorbed by the absorbent material 3, the wearer has a minimal amount of discomfort due to moisture around the wearer's urinating part.

Figure 4B:
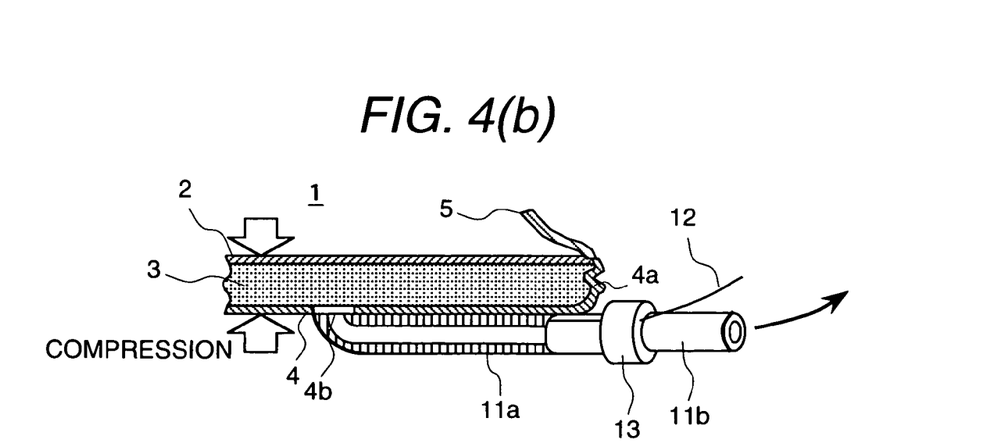

As shown in FIGS. 3, 4(a) and 4(b), at the upper end of the edge portion 4a of the outer sheet 4, three-dimensional gathers 5 are created and disposed so as to be slanted inwardly along the periphery of the outer sheet 4. These slantingly provided three-dimensional gathers 5 prevent leaks from the sides caused by the wearer's physical activity or a change of posture. In addition, as shown in FIG. 2(b), two strips of anti-slip tape (two-sided tape) 6 adhere to the outer bottom surface of the outer sheet 4. The anti-slip tape 6 adheres to the wearer's underwear to prevent the urine receptacle 1 from shifting.

One end of the urine drainage tube (a first urine drainage means) 11a is connected to the urine drainage port 4b that is formed on the bottom surface of the outer sheet 4. A one-touch joint 13 is mounted to one end of the urine drainage tube (a second urine drainage means) 11b. This joint 13 connects the other end of the urine drainage tube 11a to the end of the urine drainage tube 11b. The urine drainage tubes 11a and 11b are made of soft, flexible materials, and the one-touch joint 13 is also made of a soft material. Further, the first urine drainage means includes the urine drainage port 4b also.

A urine tank 21, which is shown in FIG. 1, is sealed by a lid 22. The other end of the urine drainage tube 11b passes through the lid 22 of the urine tank 21 and is located in the vapor phase area 21a of the urine tank 21. One end of a vacuum tube 11c is connected to a vacuum pump 31 and the other end passes through the lid 22 of the urine tank 21 and is located in the vapor phase area 21a of the urine tank 21. Like the urine drainage tubes 11a and 11b, the urine drainage tube 11c is also made of a soft, flexible material. The capacity of the urine tank 21 is about 500 $cm^3$, so that it can store two separate urinations. This tank also comes in 200 $cm^3$ or 1000 $cm^3$, sizes, which allows for prolonged use at night.

The vacuum pump 31 is driven by a motor 32. The motor 32 uses a battery 33 as a driving power source, and it is controlled by a control device installed on a control board 34. The vacuum pump 31 is small, having a is diameter of 30 mm×70 mm. The rated voltage of the battery 33 is approximately 6 V.

A urine sensor 12 detects when urine has been absorbed by the urine absorbent material 3. It is located along the urine drainage tube 11a and is turned on in the vicinity of one end of the tube 11a (near the urine drainage port 4b) when urine is discharged. The urine sensor 12 is electrically conductive and detects the wearer's urination by sensing a resistance value change therein. The urine detection signal detected by the urine sensor 12 is inputted into the control board 34 that controls the vacuum pump 31.

Figure 5:
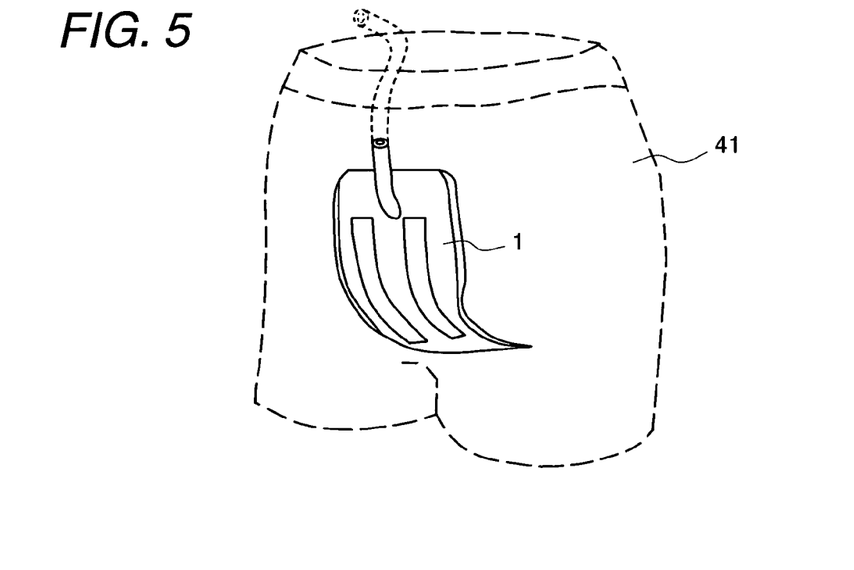
FIG. 5 is a diagrammatic perspective view which shows the condition when the urine receptacle is worn.

In this configuration, the urine receptacle 1 is worn inside the wearer's (not shown) underwear 41, as shown in FIG. 5, so that the top sheet 2 comes in contact with the wearer's urinating part. The urine tank 21, vacuum pump 31, and the motor 32 can be carried by the wearer, or they can be placed on or under the bed on which the wearer lies.

When the wearer urinates, urine that is discharged in the urine receptacle 1 is absorbed by the urine absorbent material 3 through the top sheet (non-woven fabric) 2. When urine absorbed by the urine absorbent material 3 reaches the urine drainage port 4b of the outer sheet 4, the urine sensor 12 is turned on, and a urine detection signal is inputted to the control board 34. The control device installed on the control board 34 activates the motor 32 to drive the vacuum pump 31.

When air in the urine tank 21 has been discharged by the vacuum pump 31, the air pressure in the urine absorbent material 3 decreases, creating a negative pressure in the urine drainage port 4b. Because the hard-breathable top sheet 2 and the non-breathable outer sheet 4 cover the urine absorbent material 3 and keep it substantially airtight, when air has been removed via the urine drainage tube 11a, negative pressure is also applied to the urine absorbent material 3. When negative pressure is applied to the urine absorbent material 3, a pressure difference between the an pressure in the material and the atmospheric pressure around the urine receptacle 1 causes the urine absorbent material 3 to compress, as successively shown in FIGS. 4(a) and 4(b). Contraction of the urine absorbent material 3 will squeeze the absorbed urine and direct its flow to the urine drainage port 4b. Urine directed to the urine drainage port 4b is further directed into the urine tank 21 by the negative pressure via the urine drainage tubes 11a and 11b.

The inner surface of the outer sheet 4 is designed to be water-repellent. Therefore, urine that has been squeezed from the urine absorbent material 3 and stored between the urine absorbent material 3 and the outer sheet 4 is quickly directed to the urine drainage port 4a.

The urine tank 21 can be removed by disconnecting the urine drainage tubes 11a and 11b by unlocking the one-touch joint 13. Thus, the urine tank 21 can be carried, and the urine stored therein can be disposed of. The urine receptacle 1 is replaced with a new one after the wearer has worn it for a day, and the used urine receptacle 1 is discarded.

The wearer's urine is thus disposed of. In accordance with the present invention, the urine absorbent material 3 is covered with the hard-breathable top sheet 2, and the outer sheet 4 together with the top sheet 2 keeps the urine absorbent material 3 highly airtight, so that urine can be drained by using the vacuum pump 31.

Figure 6:
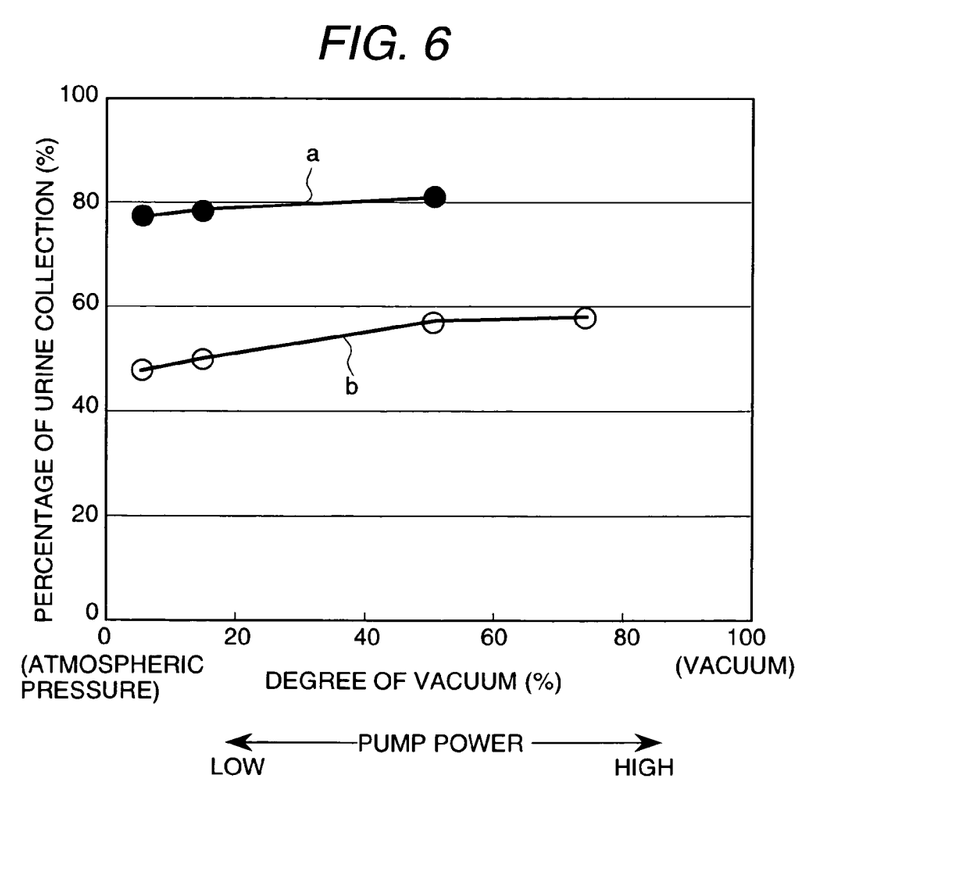
FIG. 6 is a characteristic diagram of the operation of the automatic urine disposal device.

The percentage of urine collection by the urine absorbent material 3 has been measured by operating the vacuum pump 31 for 120 seconds using the urine receptacle 1, according to the present invention, which incorporates a non-woven fabric as the top sheet 2. Characteristic <a> in FIG. 6 shows the results. The characteristic <a> proves that even a vacuum pump 31 with a low power can achieve nearly 80% of urine collection. In contrast, as indicated by characteristic <b>, a vacuum pump 31 with a high power drains only 60% of the urine from the urine absorbent material 3 when the non-breathable top sheet 2 is absent.

As stated above, in the urine receptacle used in accordance with the present invention, the surface of the urine absorbent material is covered with a liquid-permeable, hard-breathable top sheet. Therefore, as air pressure in the urine absorbent material decreases, the urine absorbent material is compressed, causing urine to be squeezed out. As a result, the percentage of urine collection increases and the amount of urine which remains in the urine receptacle is reduced. With the increase in the percentage of urine collection, a small capacity vacuum pump 31 with a low suction force can be used to drain urine from the urine absorbent material. Therefore, it is possible to drain urine from the urine receptacle without discomfort to the wearer, and the device can be compact and lightweight.

Since the device can be compact and lightweight, if it is used as a portable automatic urine disposal device, it will be most efficient. Furthermore, because the device is compact and lightweight and the vacuum pump does not unnecessarily absorb air, the noise is minimal and urine can be quietly drained without bothering other patients in the room at night.

Figure 7A:
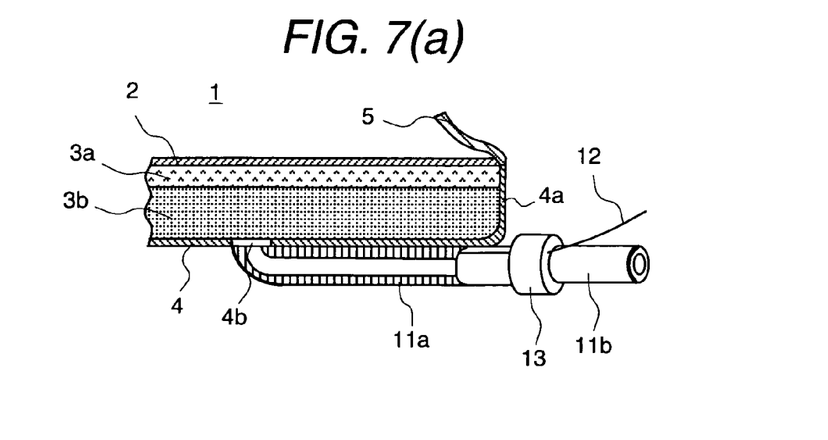
FIG. 7(a) and FIG. 7(b) are sectional views showing the urine receptacle according to another embodiment of the present invention.
Figure 7B:
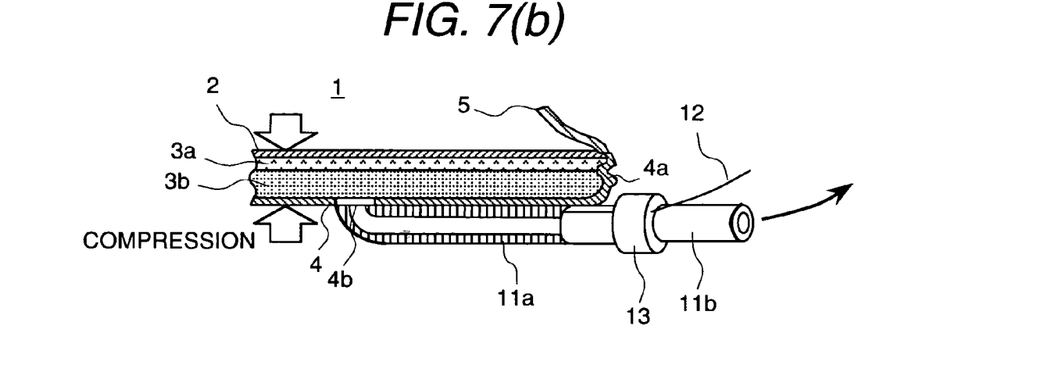

FIG. 7(a) and FIG. 7(b) show another embodiment of the urine receptacle 1, in which the urine absorbent material 3 comprises multiple layers laminated together, and more specifically, in which two layers 3a and 3b of the urine absorbent material 3a and 3b are laminated. Those two layers are laminated such that the water-absorbent capability of the urine absorbent material 3b located on the bottom surface of the outer sheet 4 is larger than that of the urine absorbent material 3a. The urine absorbent material 3a is a hydrophilic synthetic fiber tow bundle or sponge type material, and the urine absorbent material 3b is a hydrophilic foam or porous material.

According to the variety of postures which the wearer might assume, such as lying down on his/her back, lying down on his/her side, or sitting, a part of the urine absorbent material 3 will be compressed between the wearer's body and the bed or seating surface. If the wearer urinates in that situation, urine which has been discharged in the urine receptacle 1 may flow back through the top sheet 2.

By laminating the two layers 3a and 3b of urine absorbent material, as shown in FIG. 7(a), and increasing the water-absorbent capability of the bottom-layer urine absorbent material 3b, it is possible to prevent flowback of the urine absorbed in the bottom-layer urine absorbent material 3b. Furthermore, by laminating more than two layers of urine absorbent material 3, it is obviously possible to more effectively prevent the backflow of urine.

Figure 8:
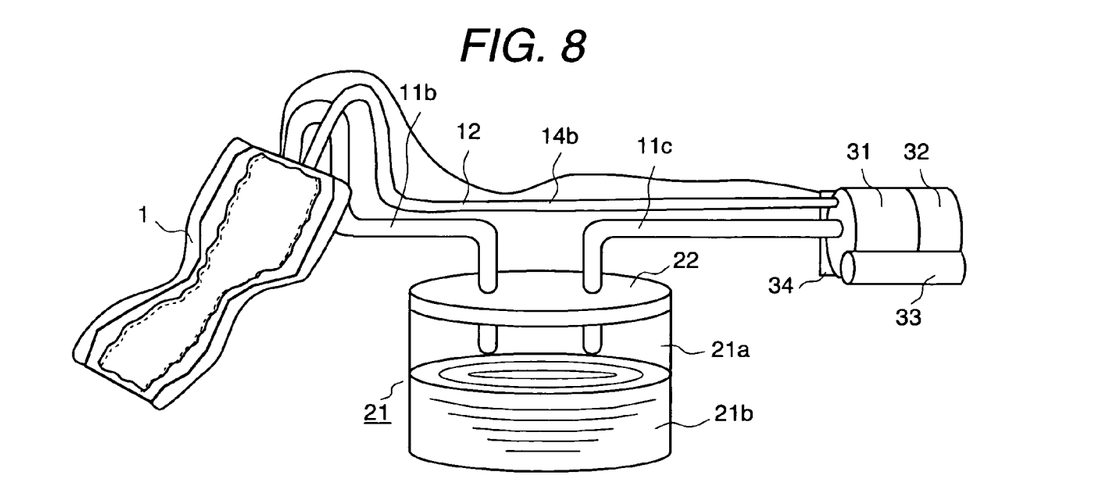
FIG. 8 is a diagram showing the urine disposal device according to a further embodiment of the present invention.
Figure 9:
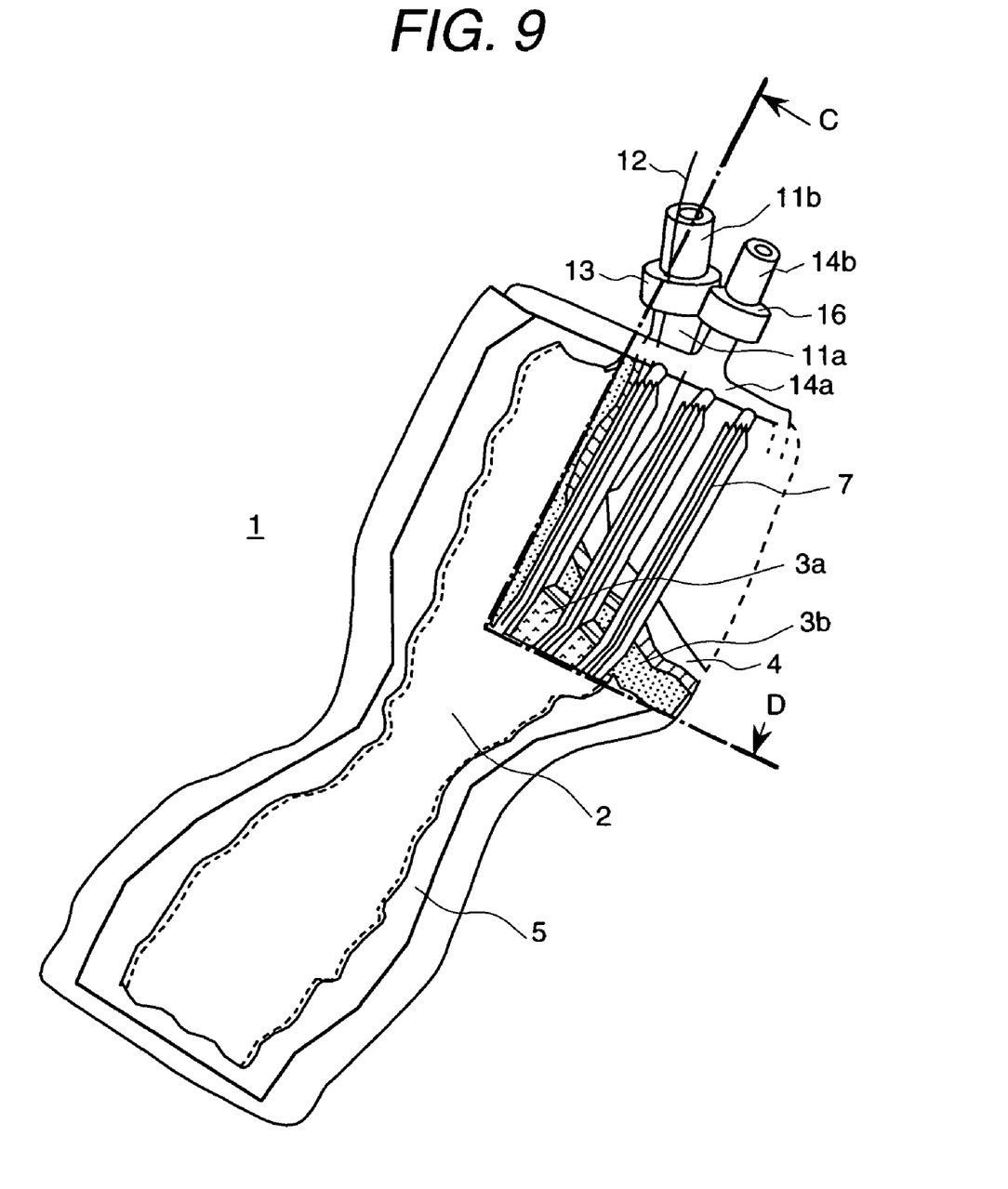
FIG. 9 is a diagram showing a further embodiment of the urine receptacle for use in the urine disposal device of FIG. 8.
Figure 10A:
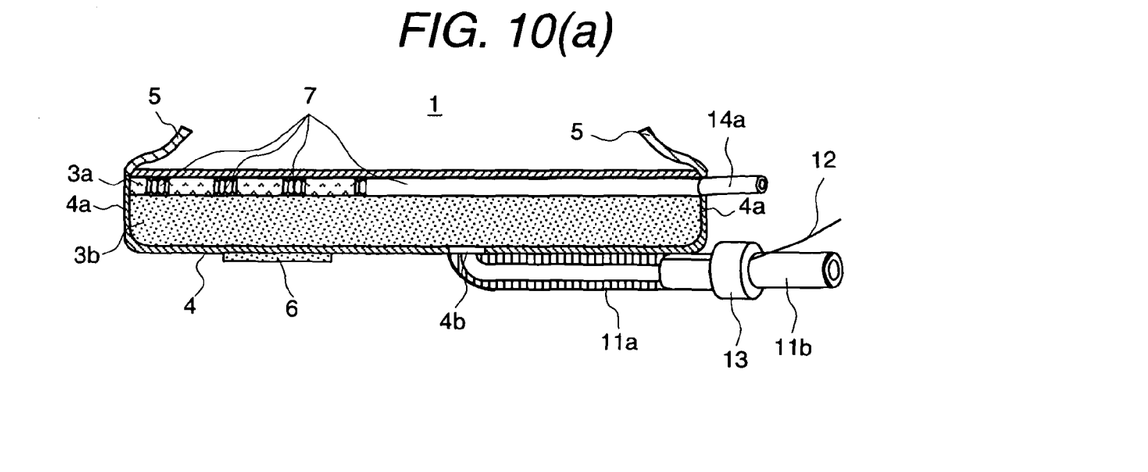
FIG. 10(a) and FIG. 10(b) are enlarged sectional views taken along the line C-D in FIG. 9.
Figure 10B:
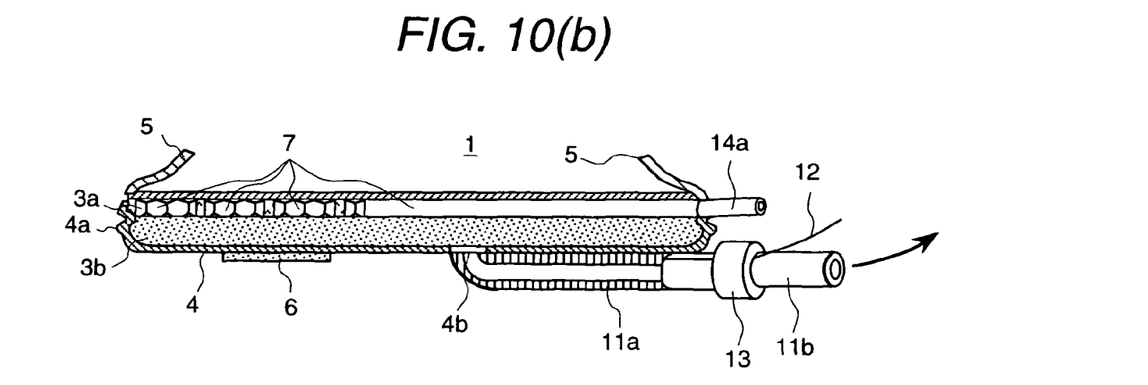

FIGS. 8 through 10(b) show another embodiment of the present invention. FIG. 8 is a diagram of an automatic urine disposal device. FIG. 9 is a block diagram partially broken away showing details of a urine receptacle, and FIGS. 10(a) and 10(b) are enlarged sectional views taken is substantially along the line C-D in FIG. 9. In FIG. 10(a), the drawing to the right side of the dot-dash line is an auxiliary cross sectional view taken in the direction of arrow C and the drawing of the left side is an auxiliary cross sectional view taken in the direction of arrow D.

The embodiment shown in FIGS. 8 through 10(b) differs from the embodiment shown in FIGS. 1 through 4(b) in that the urine absorbent material 3 of the embodiment shown in FIGS. 8 through 10(a) comprises two layers in which the upper-layer urine absorbent material 3a that comes in contact with the top sheet 2 is divided into portions in the width direction, and a plurality of accordion-folded balloons 7 are located in the spaces between the divided portions of the upper-layer urine absorbent material 3a.

As FIGS. 9 and 10(a) show, two layers 3a and 3b of the urine absorbent material of the urine receptacle 1 are laminated and are kept highly airtight by being encased in the outer sheet 4 and the top sheet 2. The upper-layer urine absorbent material 3a is divided into a plurality of portions in the width direction of the urine receptacle 1 and have spaces disposed between them.

A plurality of accordion-folded balloons 7 are placed between the divided portions of the urine absorbent material 3a in the longitudinal direction of the urine receptacle 1. The length of the balloon 7 is nearly the same as that of the urine receptacle 1 in the longitudinal direction. The balloon 7 is made of a soft flexible member, such as vinyl chloride. One end (upper side shown in FIG. 9) of a plurality of accordion-folded balloons 7 is connected to one end of an air-blast tube 14a.

The other end of the air-blast tube 14a is connected to one end of an air-blast tube 14b via a one-touch joint 16. The one-touch joint 16 is mounted to one end of the air-blast tube 14b. The other end of the air-blast tube 14b is connected to the vacuum pump 31. Furthermore, the other end of the air-blast tube 14b is connected to an exhaust port of the vacuum pump 31 when air is to be blasted into the balloons 7, and it is connected to the vacuum port of the vacuum pump 31 when air is to be discharged from the balloons 7. However, to simplify the drawings, it is shown as being connected to one location in the drawings.

When the wearer urinates while using the device of this configuration, the vacuum pump 31 is activated and urine is drained into the urine tank 21 in the same manner as the aforementioned embodiment. In that situation, the urine absorbent material 3a and the balloons 7 are in a state as shown in FIG. 10(*a*).

A control device installed on the control board 34 receives a urine detection signal from the urine sensor 12; and, after a specified time duration has passed since the vacuum pump 31 was activated, the control device connects the other end of the air-blast tube 14b to the exhaust port of the vacuum pump 31 and blasts air into the balloons 7. The time duration is determined by the time necessary for the wearer to urinate and is specified, for example, as a period of 30 seconds to 60 seconds.

The balloons 7 expand when air is blasted into them in the width direction of the urine receptacle 1. As the balloons 7 expand in the width direction, the urine absorbent material 3a is compressed, thereby the width of the urine absorbent material 3a gradually decreases. When air continues to be blasted into the balloons 7, the urine absorbent material 3a and the balloons 7 reach the state as shown in FIG. 10(*b*). A plurality of balloons 7 ultimately form barrier membranes for the urine absorbent material 3b, as shown in FIG. 10(*b*).

The upper surface of the urine absorbent material 3b is covered with the top sheet 2 and the balloons 7, which greatly increases airtightness. Accordingly, the urine absorbent material 3b is firmly compressed and urine is squeezed out, thereby increasing the percentage of urine collection and reducing the amount of urine remaining in the urine receptacle 1.

After the vacuum pump 31 has completed draining urine, the control device installed on the control board 34 connects the other end of the air-blast tube 14b to the vacuum port of the vacuum pump 31, and then the vacuum pump 31 discharges air from the balloons 7. The urine absorbent material 3a and the balloons 7 once again such the state shown in FIG. 10(*a*). Connection of the other end of the air-blast tube 14b to the exhaust port or the vacuum port of the vacuum pump 31 is usually switched by a valve.

After all the air has been discharged from the balloons 7, the vacuum pump 31 stops and the switching valve is returned to the original position, and the series of procedures is complete.

Thus, the embodiment shown in FIGS. 8 through 10(*b*), can also increase the percentage of urine collection by the urine absorbent material and reduce the amount of urine which remains in the urine receptacle. Therefore, it is possible to drain urine from the urine receptacle without discomfort to the wearer, and the device can be compact and light-weight.

Figure 11:
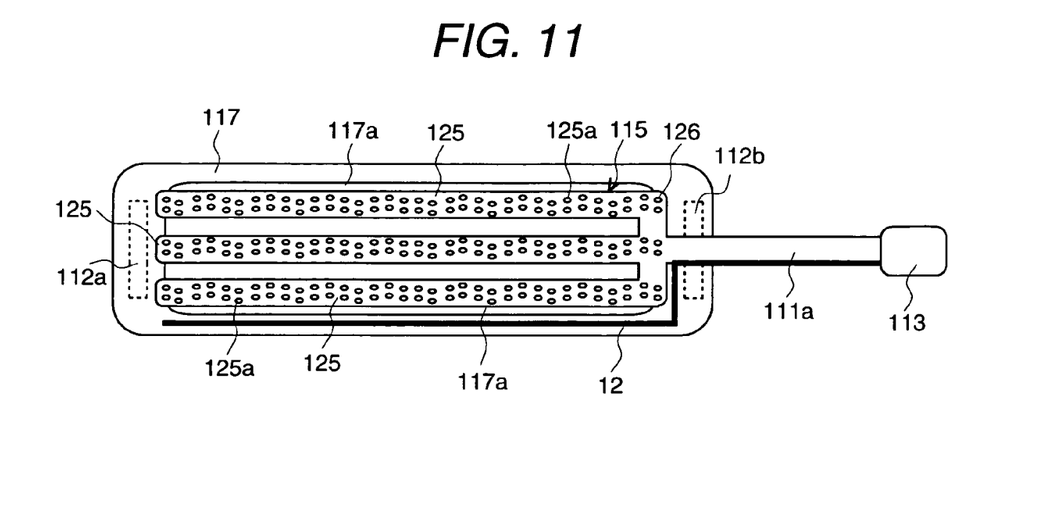
FIG. 11 is a diagrammatic plan view of a still further embodiment of a urine receptacle according to the present invention.
Figure 12:
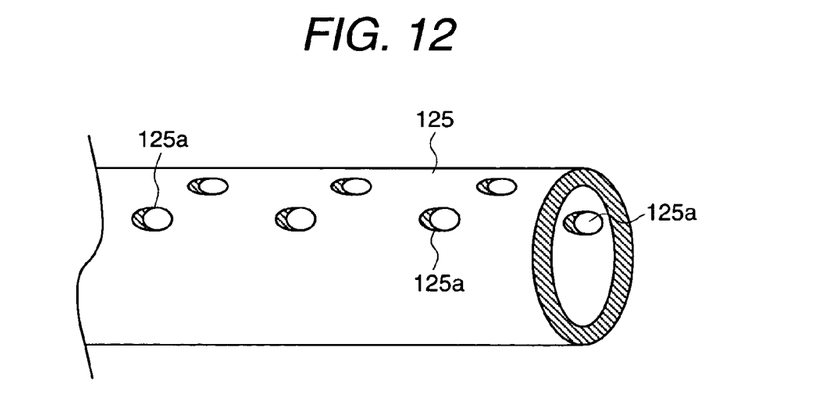
FIG. 12 is a diagram showing an enlarged view of a portion of the urine receptacle of FIG. 11.

Another embodiment of the urine receptacle in accordance with this invention will be explained with reference to FIGS. 11 and 12. In this embodiment, a perforated urine drainage tube unit 115 is located beneath the urine absorbent material. In the perforated urine drainage tube unit 115, one end of three perforated urine drainage tubes 125 are connected with a common tube 126. A urine drainage tube 111a is connected to the middle portion of the common tube 126, and the urine drainage tube 111a is connected to the vacuum pump 31 side urine drainage tube 11b. The joint 113, which is installed at the end of the urine drainage tube 111a, is connected to one end of the urine drainage tube 11b. The urine drainage tubes 111a and 11b are made of soft, flexible materials, and the one-touch joint 113 also is made of a soft material.

One end of the perforated urine drainage tubes 125 and the common tube 126 adhere to the rectangular mounting plate 117. Three perforated urine drainage tubes 125 are juxtaposed to the mounting plate 7. The perforated urine drainage tube 125 has a large number of circular urine drainage pores 125a, as shown in FIG. 12. The urine drainage pores 125a are formed on the upper half of the circumferential surface of the perforated urine drainage tubes 125.

The rectangular mounting plate 117 is made of a soft material and has a rectangular hole 117a. A pair of fixing tapes 112a and 112b is attached to the bottom surface of the rectangular mounting plate 117, and the fixing tapes 112a and 112b adhere to a support sheet located inside the outer sheet 4. The fixing tapes 112a and 112b of the mounting plate 7 adhere to the support tape on the support sheet to attach the perforated urine drainage tube unit 115 to the support sheet. Then, the top sheet 2 is attached to the support tape on the support sheet.

The three perforated urine drainage tubes 125 are held in place by the concave support sheet. The upper circumferential surface of the perforated urine drainage tube 125, on which many urine drainage pores 125a are formed, abuts on the urine absorbent material 3. That is, a large number of urine drainage pores 125a abut on the urine absorbent material 3 so as to absorb urine from the urine absorbent material 3.

According to this embodiment, the urine receptacle discharges urine that has been absorbed by the urine absorbent material through many urine drainage pores formed on the perforated urine drainage tubes. Therefore, the percentage of urine collection by the urine receptacle is increased, and the amount of urine which remains in the urine receptacle is reduced. With the increase in the percentage of urine collection, a small capacity vacuum pump with a low power can be used to drain urine from the urine absorbent material. As a result, it is possible to drain urine from the urine receptacle without discomfort to the wearer, and the device can be compact and lightweight.

Since the device can be compact and lightweight, if it is used as a portable automatic urine disposal device, it will be most efficient. Furthermore, because the device is compact and lightweight and the vacuum pump does not unnecessarily absorb air, noise is minimal and the urine can be quietly drained without bothering other patients in the room at night.

As stated above, the present invention can increase the percentage of urine collection by the urine receptacle's urine absorbent material and reduce the amount of urine which remains in the urine receptacle. With the increase in the percentage of urine collection, a small capacity vacuum pump with a low power can be used to drain urine from the urine absorbent material. Therefore, it is possible to drain urine from the urine receptacle without discomfort to the wearer, and the device can be compact and lightweight.

Since the device can be compact and lightweight, if it is used as a portable automatic urine disposal device, it will be most efficient. Furthermore, because the vacuum pump does not unnecessarily absorb air, noise is minimal and urine can be quietly drained without bothering other patients in the room at night.

Moreover, in the aforementioned embodiments, both the outer sheet and the top sheet are non-breathable or hard-breathable. However, if airtightness of the urine absorbent material is increased, the same effect can be expected when those sheets are slightly breathable.

What is claimed is:

1. An automatic urine disposal device comprising a urine receptacle having an outer sheet having a U-shaped cross-section, including at least a bottom portion and side edge portions, the bottom portion having a width at a middle portion in the longitudinal direction narrower than a width at end portions in the longitudinal direction so that it is shaped like an hourglass in plain view so as to fit a wearer's crotch, and having a gather provided along its periphery, formed of a liquid-impermeable and non-breathable thin sheet made of soft flexible material, an inner surface of which is water-repellent-finished; urine absorbent material for storing urine accommodated in said outer sheet, said urine absorbent material having at least two layers such that the water-absorbent capability of a bottom layer located adjacent said bottom portion of said outer sheet is larger than that of a top layer, said bottom layer being formed by a foam or porous material; and a top sheet formed as a liquid-permeable non-woven fabric, covering the top layer of said urine absorbent material and, with said outer sheet, keeping said urine absorbent material highly airtight, a surface of said top sheet being adapted to be in contact with a wearer's urinating part and surrounding skin, wherein said top sheet has breathability measured according to breathability testing method A, prescribed in JIS L 1096, 6.27.1, from 20 to 200 cc/cm2/second when the top sheet is dry and from 0 to 100 cc/cm2/second when the top sheet is moist and a urine drainage port provided on the bottom portion of said outer sheet; a sealed urine tank; a first urine drainage tube having one end connected to said urine drainage port; a second urine drainage tube made of soft flexible material having one end connected to another end of said first drainage tube by a one-touch joint made of a soft material and having another end operably connected to said sealed urine tank; a vacuum pump for decreasing air pressure in said sealed urine tank; and a urine sensor provided along said first urine drainage tube and electrically conductive in response to detecting a urination in the vicinity of said urine drainage port, and provided for applying a urine detection signal to a control board for controlling said vacuum pump, wherein said urine sensor detects a wearer's urination, the urine detection signal initiates said vacuum pump to deflate said urine absorbent material and extract urine, thereby discharging said urine from said urine absorbent material through said first urine drainage, said one-touch joint and said second urine drainage tube to said sealed urine tank.

2. An automatic urine disposal device of claim 1, wherein the capacity of said urine tank ranges from 200 $cm^3$ to 1000 $cm^3$.

3. An automatic urine disposal device of claim 1, wherein said urine absorbent material is 5 mm thick and is designed to absorb approximately 500 $cm^3$ of urine.

* * * * *